US00PP10629P

United States Patent [19]

Olesen et al.

[11] Patent Number: Plant 10,629

[45] Date of Patent: Oct. 6, 1998

[54] MINIATURE ROSE PLANT NAMED 'POULBAO'

[75] Inventors: L. Pernille Olesen; Mogens N. Olesen, both of Fredensborg, Denmark

[73] Assignee: Poulsen Roser ApS, Fredensborg, Denmark

[21] Appl. No.: 831,482

[22] Filed: Mar. 31, 1997

[51] Int. Cl.[6] ..... A01H 5/00

[52] U.S. Cl. ..... Plt./10

[58] Field of Search ..... Plt./10

[56] References Cited

PUBLICATIONS

UPOV–ROM, 1997/03, Plant Variety Database, GTI Jouve Retrieval Software, citation for 'POULbao'.

*Primary Examiner*—Howard J. Locker

[57] ABSTRACT

A new red miniature rose plant which has an extremely compact habit, abundant non-fading flowers and very good keepability. The variety successfully propagates from softwood cuttings and is suitable for year round production in commercial glasshouses. This new and distinct variety has shown to be uniform and stable in the resulting generations from asexual propagation.

2 Drawing Sheets

SUMMARY OF THE INVENTION

The present invention constitutes a new and distinct variety of miniature rose plant which was developed in a controlled crossing between RUImired (U.S. Plant Pat. No. 5,770) and an unnamed seedling. The two parents were crossed and the resulting seed was planted in a controlled environment. The new variety is named 'POULbao'.

The objective of the hybridization of this rose variety for commercial greenhouse culture was to create a new and distinct variety with:

1. Uniform and abundant flowers with excellent keepability, up to 14–18 days;

2. Extremely compact growth, thereby making the variety suitable for production in pot sizes of 6 cm in diameter;

3. Year-round flowering under glasshouse conditions;

4. Suitability for production from softwood cuttings in pots;

5. Durable flowers and attractive long lasting foliage which make a variety suitable for distribution in the floral industry.

This combination of qualities is not present in previously available commercial cultivars of this type and distinguish 'POULbao' frm all other varieties of which we are aware.

The seeds from the hybridization were germinated and evaluations were conducted of the resulting rose plants in a controlled environment. 'POULbao' was selected as a single plant from the progeny of the stated cross.

'POULbao' was selected by L. Pernille and Mogens N. Olsen in their rose development program in Fredensborg, Denmark in June, 1993.

Asexual reproduction of 'POULbao' by cuttings was first done by L. Pernille and Mogens N. Olesen in August, 1993. This initial and subsequent propagations have demonstrated that the characteristics of 'POULbao' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers, leaves, stems, and a plant of 'POULbao'.

Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

Specifically illustrated in SHEET 2 is the new cultivar grown in a 6 cm pot.

DETAILED DESCRIPTION OF THE VARIETY

The following is a detailed description of 'POULbao', as observed in its growth in glasshouses in Fredensborg, Denmark and Half Moon Bay, Calif. and in a field nursery in Applegate, Oreg. Descriptions were made from plants treated with growth regulators normally used in the greenhouse production process. The growth regulator Paclobutrazol was applied at 15 ppm weekly for three weeks beginning at a plant age of 6 weeks. The peduncle lengths mentioned may actually be shorter and the foliage color several shades darker than on untreated specimens. Color references are made using The Royal Horticultural Society (London, England) Colour Chart, 1995.

For a comparison, the nearest existing rose variety is POULvok, a patented variety described and illustrated in U.S. Plant Pat. No. 9,090 and issued on Mar. 28, 1995. Chart 1 details several physical characteristic of the presently disclosed and the comparison cultivar.

CHART 1

| Characteristic | 'POULbao' | 'POULvok' |
|---|---|---|
| Color of upper side of petals | RHS 43A of the Red Group | RHS 44A of the Red Group |
| Color of reverse side of petals | RHS 46D of the Red Group | RHS 44A of the Red Group |

Parents: RUImired×Unnamed seedling.

Classification:

*Botanical.*—*Rosa hybrida.*

*Commercial.*—Miniature.

Flower and Flower Bud

Blooming cycle: Recurrent.

Flower bud:

*Size.*—10 mm in length when petals are just begining to crack open.

*Bud form.*—Ovoid.

*Bud color.*—R.H.S. 46 C of the Red Color Group at ¼ opening.

*Sepals.*—R.H.S. 137 B of the Green Group. Foliaceous appendages on three of the five sepals. Surfaces of sepals moderately pubescent. Hairs present on edges of sepals with appendages.

*Peduncle.*—Surface: Hairs present on entire length. Length: 20–25 mm average length. Color: R.H.S. 137 C of the Green Group. Prickles: Not present.

*Receptacle.*—Surface: Smooth. Shape: Urn shaped. Size: Small 4 mm×5 mm. Color: 138 A of the Green Group.

*Borne.*—Upright. Generally with 1–5 buds per flowering stem.

Flower bloom:

*Diameter.*—Small. 25–28 mm. on average.

*Form.*—Upon opening, urn shaped. Completely open bloom flattened, with petals reflexing somewhat.

*Petalage.*—Double. Average range: 18–20.

*Color.*—Upon opening, the upper surface is R.H.S. 43 A of the Red Color Group. Upon opening, the reverse side is R.H.S. 46 D of the Red Color Group. After opening, the upper surface is R.H.S. 43 A of the Red Color Group. After 5–7 days open, color fades only slightly to 43 B of the Red Group. After opening, the reverse surface is R.H.S. 46 D of the Red Color Group. After 5–7 days open, color fades slightly to 47 D of the Red Group. A small spot exists on the inner side of the petal base, with a color of R.H.S. 155 B of the White Group. A small spot exists on the outer side of the petal base, with a color of R.H.S. 155 B of the White Group.

*Reflex.*—Petals reflex backwards slightly.

*Petal edge.*—Uniform.

*Fragrance.*—None.

*Duration.*—Long lasting, up to 14–18 days.

Reproductive organs:

*Pollen.*—Yellow. Yellow Group 13B. Moderately abundant.

*Anthers.*—Size: Large. Color: Yellow-brown. Yellow-Orange Group 22A.

*Filaments.*—Color: Yellow-Green Group 154C. Length: Short.

*Stigmas.*—Slightly superior in location in reference to anthers. Yellow-Green Group 154D.

*Styles.*—Color: White.

Plant

Plant growth: Compact and bushy. When grown as a 6 cm pot plant, the average height of the plant itself is 8–10 cm and the average width is 8–10 cm. When grown as a nursery plant on its own roots the average plant height is 15–20 cm and the average plant width is 15–20 cm.

Stems:

*Color.*—Young wood: Green. Yellow-Green Group 144B. Older wood: Green. Green Group 138A.

*Thorns.*—Incidence: Few thorns. Size: Average length: to 3 mm. Color: On upper portion of stems Yellow-Green Group 145D. Greyed-Yellow Group 161A on lower thorns. Shape: Linear.

*Bark.*—Young wood: Smooth. Older wood: Smooth.

Plant foliage:

*Normal number of leaflets on average leaves.*—5 leaflets.

*Leaf size.*—Small. 30 mm×45 mm.

*Abundance.*—Average.

*Color.*—Top: Dark green. R.H.S. 137 A of the Green Color Group. Bottom: Medium green. R.H.S. 138 A of the Green Color Group. Juvenile foliage: Green. Green Group 143A. Mature Foliage: Medium green. Color group 137 A of the Green Color Group.

Plant leaves and leaflets:

*Stipules.*—Present. Short, bearded. Green Group 137A.

*Petiole.*—Length: 10–12 mm. Underneath: With prickles. Color: Green Group 137C. The petiole rachis has stiff hairs.

*Edge.*—Finely serrated.

*Shape.*—Leaflets are ovate.

*Leaflets.*—Number: 5.

*Other.*—Semi-glossy. Thin texture.

Disease resistance: Resistant to mildew, rust, black spot, Botrytis under normal growing conditions in Half Moon Bay and Fredensborg, Denmark.

We claim:

1. A new and distinct variety of rose plant of the miniature class, substantially as herein illustrated and described, as a distinct and novel rose variety due to its abundant flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

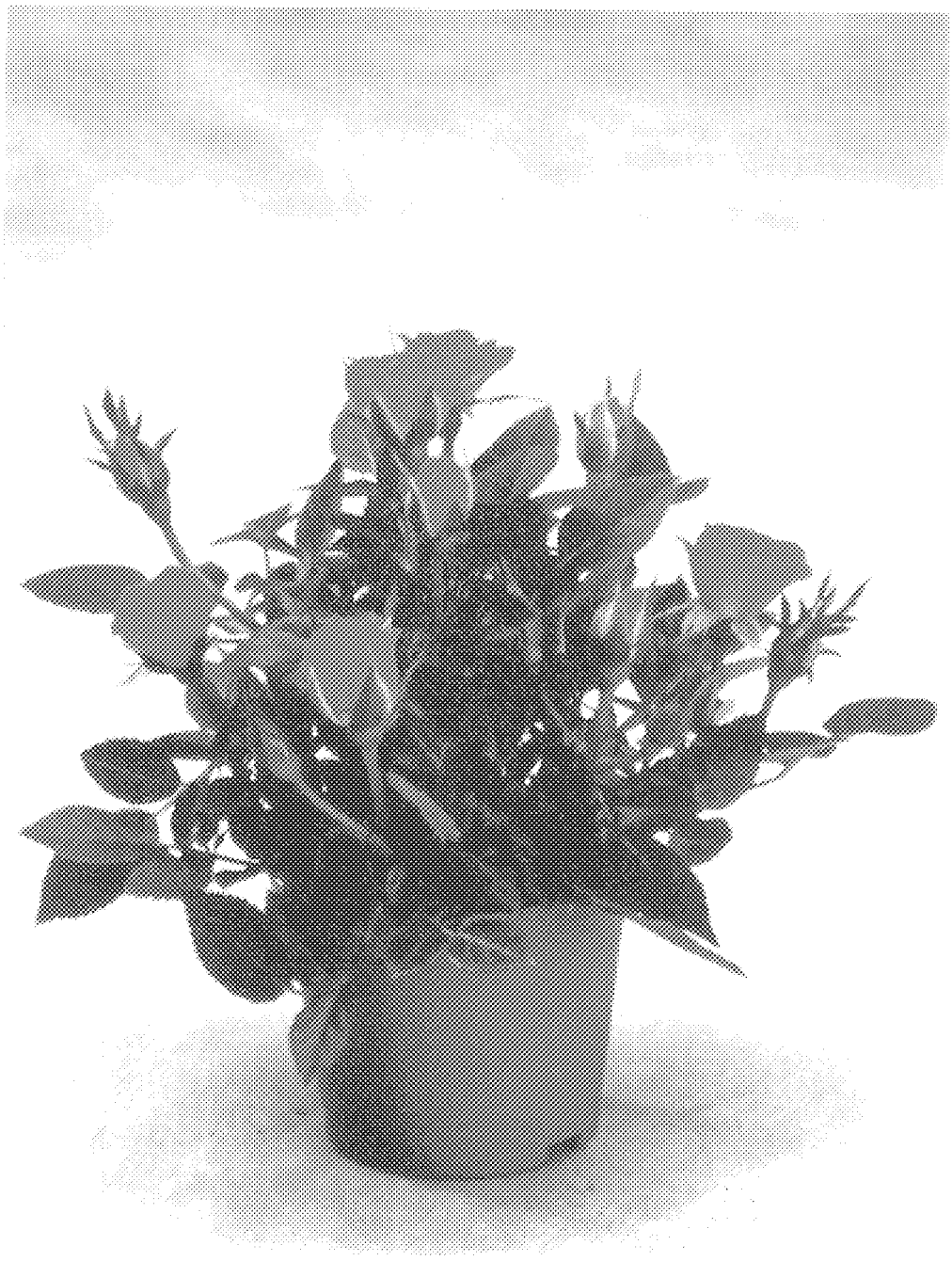

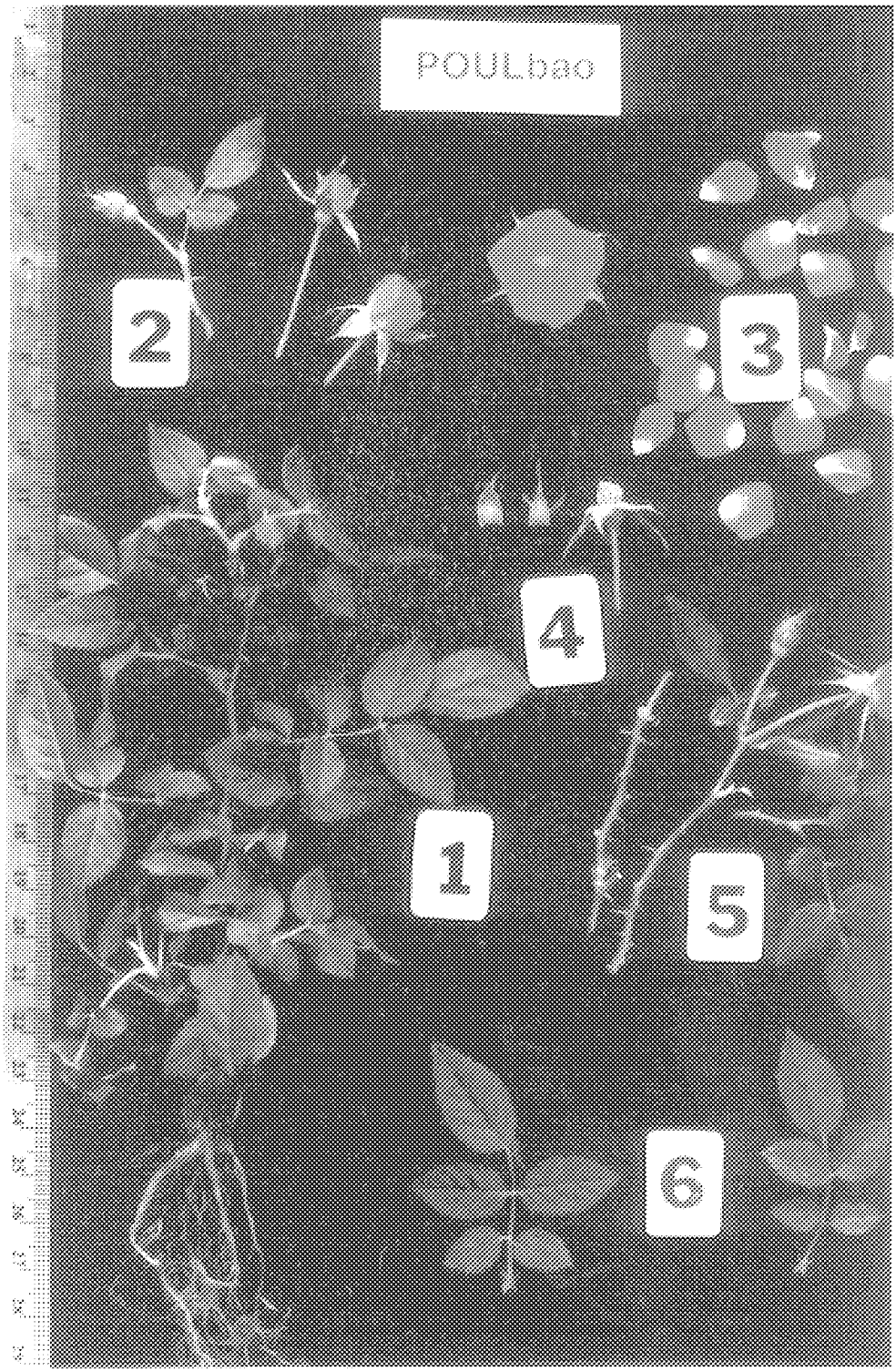
POULbao
2
3
4
1
5
6